US007582443B2

(12) United States Patent
Cavanaugh

(10) Patent No.: US 7,582,443 B2
(45) Date of Patent: Sep. 1, 2009

(54) METHOD FOR THE DETECTION AND MEASUREMENT OF HAPTEN-CONJUGATED BIOLOGICAL BINDING ENTITIES BY WESTERN AND DOT-BLOT USING ANTI-HAPTEN ANTIBODIES

(76) Inventor: Philip Gerard Cavanaugh, 26215 Ivanhoe, Redford, MI (US) 48239

( * ) Notice: Subject to any disclaimer, the term of this patent is extended or adjusted under 35 U.S.C. 154(b) by 0 days.

(21) Appl. No.: 10/002,690

(22) Filed: Dec. 5, 2001

(65) Prior Publication Data

US 2002/0132256 A1 Sep. 19, 2002

(51) Int. Cl.
*C12Q 1/06* (2006.01)
*C12Q 1/00* (2006.01)
*G01N 33/53* (2006.01)
*G01N 33/00* (2006.01)
*C12N 13/00* (2006.01)

(52) U.S. Cl. ............... 435/39; 435/4; 435/7.1; 435/7.2; 435/7.71; 435/7.8; 435/7.9; 435/7.93; 435/7.94; 435/7.95; 435/173.4; 435/173.7; 435/173.9; 436/8; 436/501; 436/513; 436/518; 436/532

(58) Field of Classification Search .................. 435/4, 435/7.1, 7.2, 7.21, 7.71, 7.93, 174, 176, 177; 436/501, 507, 512, 513, 515, 516, 518, 530, 436/532, 538, 546

See application file for complete search history.

(56) References Cited

U.S. PATENT DOCUMENTS

| 5,576,436 | A | 11/1996 | McCabe et al. |
| 5,962,223 | A | 10/1999 | Whitely et al. |
| 6,027,890 | A | 2/2000 | Ness et al. |
| 6,054,557 | A | 4/2000 | Faure |
| 6,815,212 | B2 | 11/2004 | Ness et al. |

OTHER PUBLICATIONS

Cavanaugh et al. 1998. J. of Cell. Physio. 174:48-57.*
Lagrange, J.L. et al., "Demonstration and characterization of EGF receptors in cancer of the uterine cervix", Bull Cancer, 1993, 80: 219-224. ABS.
Inoue, T. et al., "Differences in transferrin response and numbers of transferrin receptors in rat and human mammary carcinoma lines of different metastatic potentials", Journal of Cellular Physiology, 1993, 156: 212-217.

(Continued)

*Primary Examiner*—Mark Navarro
*Assistant Examiner*—JaNa Hines

(57) ABSTRACT

The invention is a procedure for measuring the binding of an entity (ligand) to a surface by using a hapten-conjugated version of the ligand (hapten-ligand). An excess of the hapten-ligand is presented to the binding surface and excess (unbound) hapten-ligand is washed off. Bound hapten-ligand is then solubilized (removed) and applied to a membrane support or separated by electrophoresis and applied to a membrane support. Known amounts of hapten-ligand are similarly applied to the membrane, to provide for hapten-ligand standards. The membrane-bound hapten-ligand is detected by application of an enzyme-conjugated antibody to the hapten; or by application of an antibody to the hapten followed by application of an enzyme-conjugated antibody to the anti-hapten antibody. The resultant membrane-associated enzyme is detected and quantitated by the application of a color or light-producing substrate which reacts with the enzyme. A combination of the use of anti-hapten antibodies along with membrane-blotting technologies to assess hapten-ligand binding to surfaces is not found in the scientific or patent literature, particularly in regards to assessing protein binding to cell surfaces.

20 Claims, 10 Drawing Sheets

OTHER PUBLICATIONS

Cavanaugh, P.G., and Nicolson, G.L., "The selection of a metastatic rat mammary adenocarcinoma cell line from a low metastatic parental population by an in vitro process based on cellular ability to proliferate in response to transferrin", Journal of Cellular Physiology, 174, 48-57, 1998.

Cavanaugh, P.G., et al., "Transferrin receptor overexpression enhances transferrin responsiveness and the metastatic growth of a rat mammary adenocarcinoma cell line", Breast Cancer Research and Treatment, 56, 203-217, 1999.

Gordon, I.L. "Scatchard analysis of fluorescent concanavalin A binding to lymphocytes", Cytometry, 1995, 20, 238-244.

Palupi, N.S. et al., "Bovine beta-lactoglobulin receptors on transformed mammalian cells (hybridomas MARK-3): characterization by flow cytometry", J Biotechnol, 2000, 78, 171-184.

Samuel D. et al., "A sensitive method of detecting proteins on dot and Western blots using a monoclonal antibody to FITC", J Immunol Methods, 1988, 107, 217-224.

Haselback, A. et al., "Structural characterization of glycoprotein carbohydrate chains by using digoxygenin-labeled lectins on blots", Analytical Biochemistry, 1990, 191, 25-30.

Haselback, A and Hosel, W. "Detection of proteins and glycoproteins on western blots", in "Nonradioactive labeling and detection of biomolecules", Kessler, C., ed., 1992, 297-299, Springer-Verlag, Berlin.

Zhang, G., et al., "Early detection of apoptosis using a fluorescent conjugate of annexin V", Biotechniques, 1997, 23, 525-531.

Le Gall M., et al., "The p42/p44 MAP kinase pathway prevents apoptosis induced by anchorage and serum removal", Mol Biol Cell, 2000, 11, 1103-1112.

Niedergang F., et al. "Convulxin binding to platelet receptor GPVI: competition with collagen related peptides", Biochem Biophys Res Commun, 2000 273, 246-250.

Schaffer, L. "A model for insulin binding to the insulin receptor", Eur J Biochem, 1994, 1127-1132.

Schagger H, von Jagow G. Tricine-sodium dodecyl sulfate-polyacrylamide gel electrophoresis for the separation of proteins in the range from 1 to 100 kDa Anal Biochem., 1987,166,:368-379.

Cavanaugh, P.G. and Nicolson, G. L. "Lung derived growth factor that stimulates the growth of lung-metastasizing tumor cells: Identification as transferrin", Journal of Cellular Biochemistry, 47:261-271, 1991.

Cavanaugh, P.G., and Nicolson, G.L., "The selection of a metastatic rat mammary adenocarcinoma cell line from a low metastatic parental population by an in vitro process based on cellular ability to proliferate in response to transferrin", Journal of Cellular Physiology, 174: 48-57, 1998.

Cavanaugh, P.G., Jia, L., and Nicolson, G.L. , "Transferrin receptor overexpression enhances transferrin responsiveness and the metastatic growth of a rat mammary adenocarcinoma cell line", Breast Cancer Research and Treatment, 56:203-217, 1999.

Chaudary, S., Das, S., BanerJee, S.K.,, and Sarker, P.K. "Identification and characterization of a tubuline binding protein in rat brain plasma membrane", Neurochem Int, 1994, 24, 289-299.

Darzynkiewicz Z, Bedner E, Traganos F, Murakami T, "Critical aspects in the analysis of apoptosis and necrosis", Hum Cell, 1998, 11, 3-12.

Gordon, I.L. "Scatchard analysis of fluorescent concanavalin A binding to lymphocytes", Cytometry, 1995, 20, 238-244.

Inoue, T., Cavanaugh., P. G., Steck, P. A., and Nicolson, G. L., "Differences in transferrin response and numbers of transferrin receptors in rat and human mammary carcinoma lines of different metastatic potentials", Journal of Cellular Physiology, 156: 212-217, 1993.

Lagrange JL, Francoual M, Formento JL, Del Guidice P, Bensadoun RJ, Teissier E, Ettore F, Gillet JY, Namer M, Milano G, "Demonstration and characterization of EGF receptors in cancer of the uterine cervix", Bull Cancer, 1993, 80, 219-224.

Le Gall M, Chambard JC, Breittmayer JP, Grall D, Pouyssegur J, Van Obberghen-Schilling E, "The p42/p44 MAP kinase pathway prevents apoptosis induced by anchorage and serum removal", Mol Biol Cell, 2000, 11, 1103-1112.

Niedergang F, Alcover A, Knight CG, Farndale RW, Barnes MJ, Francischetti IM, Bon C, Leduc M, "Convulxin binding to platelet receptor GPVI: competition with collagen related peptides" Biochem Biophys Res Commun, 2000 273, 246-250.

Palupi NS, Franck P, Guimont C, Linden G, Dumas D, Stoltz J, Nabet P, Belleville-Nabet F, Dousset B, "Bovine beta-lactoglobulin receptors on transformed mammalian cells (hybridomas MARK-3): characterization by flow cytometry", J Biotechnol, 2000, 78, 171-184.

Samuel D, Patt RJ, Abuknesha RA, "A sensitive method of detecting proteins on dot and Western blots using a monoclonal antibody to FITC", J Immunol Methods, 1988, 107, 217-224.

Scacchi GE, Turyn D, Dellacha JM, "Identification of insulin binding sites in isolated cells from rat submaxillary gland", Arch Biol Med Exp (Santiago), 1988, 21,189-193.

Zhang G, Gurtu V, Kain SR, Yan G, "Early detection of apoptosis using a fluorescent conjugate of annexin V", Biotechniques 1997, 23, 525-531.

* cited by examiner

METHOD FOR THE DETECTION AND MEASUREMENT OF HAPTEN-CONJUGATED BIOLOGICAL BINDING ENTITIES BY WESTERN AND DOT-BLOT USING ANTI-HAPTEN ANTIBODIES

STATEMENT REGARDING FEDERALLY SPONSORED RESEARCH OR DEVELOPMENT

This invention was not directly supported by any federally sponsored research.

CROSS REFERENCE TO RELATED APPLICATIONS

None

REFERENCE TO SEQUENCE LISTING, TABLES, OR COMPUTER PROGRAM LISTINGS

None

BACKGROUND OF THE INVENTION

Frequently, researchers desire to analyze the ability of various proteins and other factors to bind to cell surfaces. Usually, the type of binding studied is one where the binding factor (ligand) recognizes and binds to a specific receptor for it on the cell surface. Thus, these types of studies are used to examine the inherent properties of the ligand itself, but also are used solely to study the receptor. Analysis of ligand binding to cell surfaces is usually performed directly, wherein that ligand itself is obtained in pure form and is radiolabeled. Usually, ligands are radiolabeled with $^{125}$I. More rarely, they are purchased labeled with $^3$H or $^{14}$C. The labeled ligand is assessed for its maintenance of activity, and for its specific (cpm per unit of weight) radioactivity. To measure binding, the radiolabeled material is applied under established optimal conditions to desired cells of known density (cells/unit volume or cell protein/unit volume). Typically, various concentrations (from high to low) of the ligand are added to separate tubes or dishes of cells. Certain cell containers at each dose tested also receive an excess of unlabeled pure ligand. Usually, these excesses are 10-200 fold times the concentration of labeled ligand. After the desired binding time has passed, the unbound material from all samples is saved and the cells are washed free of all unbound labeled and unlabeled ligand. The cells are then placed into counting tubes and counted for radioactivity. Initial unbound material is counted also. The amount of labeled ligand bound or unbound is calculated from the known specific cpm. Counts obtained from unlabeled excess ligand-receiving samples are subtracted from the counts obtained from samples treated with like-dose labeled ligand only. This provides specific cpm bound. The weight amount of specific labeled ligand bound is calculated from the known specific cpm per unit weight. Knowing the cell density, one can calculate amount of specific ligand bound per cell at each ligand dose level. Usually, the data is plotted as specific ligand bound/ligand unbound/unit of cells on the y axis and specific ligand bound/unit of cells on the x axis. This produces data with a negative slope and the x-intercept is the maximum amount of ligand able to bind. Therefore, the x-intercept also represents the receptors/cell for the ligand. This type of analysis is referred to as a Scatchard analysis. (Inoue et. al., 1993; LaGrange et. al., 1993; Schaffer, 1994; Gordon, 1995; Cavanaugh and Nicolson, 1998; Cavanaugh et. al., 1999).

An alternative method to determine ligand binding to cells is to conjugate a particular fluorescent molecule to the pure ligand. Fluorescent labeled material is allowed to bind to cells at various concentrations with or without the presence of unlabeled ligand. After binding is complete, all unbound ligand is washed off and the fluorescence of the cells is determined using a fluorescent spectrophotometer or a fluorescent activated cell sorter instrument (Gordon, 1995; Niedergang et. al., 2000; Palupi et. al., 2000, U.S. Pat. Nos. 5,576,436, 5,962,223, 6,027,890, 6,815,212). This procedure is more difficult to standardize and precise quantitation of ligand receptors/cell is not as accurate as with Scatchard analysis using radiolabeled ligand. This method is more given to comparing binding capacity between two different cell populations. With fluorescent activated cell sorting, it also requires that the binding surface exist in a monodispersed state capable of being analyzed in the flow cell of that instrument.

It is also possible to allow ligand binding to cell surfaces and to then incubate the cells with a fluorescent labeled antibody to the ligand, wash, and analyze cell fluorescence by fluorescent spectrophotometry or fluorescent activated cell sorting. To assess ligand receptor levels only, one can incubate cells with a fluorescent labeled antibody to the receptor and measure the fluorescence of the cells by fluorescent activated cell sorting (Cavanaugh and Nicolson, 1998; Cavanaugh et. al., 1999).

Western blotting is a technique where cell lysates obtained by detergent treatment are separated by electrophoresis and the separated components contained within the electrophoresis gel are driven onto a protein-binding membrane via electric current. The membrane with its cell constituents separated by molecular weight is blocked with a non-specific protein and can than be analyzed for particular cellular constituents by treatment with an antibody to that constituent followed by treatment with an enzyme conjugated antibody to the first antibody. Enzyme containing regions of the membrane are detected using color-producing or light-emitting substrates for that enzyme.

Dot-blotting or slot-blotting is where the cell lysate is applied directly to a binding-membrane without prior separation by electrophoresis. The membrane is blocked and treated as described in the previous paragraph to detect particular cell constituents. Unlike Western-blotting, the molecular weight of detected material is not ascertained.

We found that the binding of transferrin to tumor cell surfaces correlated with the aggressiveness of those cells; i.e.: the more metastatic tumor cells bound more transferrin than did poorly metastatic cells (Cavanaugh and Nicolson, 1991, Cavanaugh and Nicolson, 1998; Cavanaugh et. al., 1999). These studies required that we accurately assess the transferrin binding capability of cells in question. Initially, this was performed by examining the ability of the cells to bind $^{125}$I-transferrin and the ability of non-labeled transferrin to inhibit that. Dealing with radioactive iodine has many drawbacks including the inherent hazardous nature of the material, its short shelf life, and expensive waste disposal. In searching for novel methods for measuring transferrin binding using non-radioactive procedures, we came upon the discovery that fluorescein-labeled transferrin would stimulate the growth of cells in culture similarly to native transferrin. We also found that fluorescein-labeled transferrin could be internalized by cells and that this internalization could be competed for by an excess of un-labeled (or native) transferrin. The apparent retention of biological activity by fluorescein-labeled transferrin lent us to examine other technologies available to specifically detect the labeled protein. Many antibody suppliers now sell anti-fluorescein antibodies. These were initially developed to detect fluorescein-labeled oligonucleotides hybridized to sample RNA on Northern blots. These same antibodies can easily detect fluorescein-labeled proteins on Western blots (Samuel et. al.; 1988, Haselbeck, et al., 1990, Haselbeck and Hosel, 1992). We next assessed as to whether or not the combination of these reagents together would allow for the detection of fluorescein-labeled protein bound to cell surfaces. Cells were treated with fluorescein-labeled transferrin with and without an excess of native transferrin. After an appropriate incubation period, the cells were washed extensively and lysed with a detergent containing buffer. The lysate components were separated by electrophoresis and electroblotted onto a nitrocellulose membrane. The membrane was blocked with non-fat dry milk and incubated with a rabbit anti-fluorescein antibody. The membrane was washed and incubated with goat horse radish peroxidase-conjugated anti-rabbit IgG. The membrane was washed again and treated with a light emitting (enhanced luminescence) substrate for horse radish peroxidase. One band at ≈70,000 in molecular weight was seen in all lanes loaded with cells that initially were exposed to fluorescein-labeled transferrin only. In lanes loaded with cells that had also received an excess of native transferrin, a markedly reduced band, or no band at all was seen. This method allowed for the sensitive determination of transferrin binding to cells without the need for radioactively labeled transferrin. Furthermore, the molecular weight of the bound ligand was verified via the electrophoresis step.

The major difference in the method of this ligand binding method in comparison to those of the referenced patents and literature papers is the final detection method. In our case, the bound hapten-ligand is detected by immunological means after solubilization (or cell lysis) and immobilization onto a membrane. In the referenced cases, bound radio-labeled ligand is detected on solubilized cells by counting; or in the case of fluorescent-labeled ligands, by fluorescent detection of the label on intact cells by optical means such as cytometry.

BRIEF SUMMARY OF THE INVENTION

The present invention relates to the need in biological research to measure the ability of cells or other surfaces to bind a given compound (hereafter referred to as a ligand). The ligand could be a growth factor or any other factor whose study involves the need for persons to assess the ability of cells, or any other insoluble particle or material, to bind it. The invention requires that the binding factor be conjugated with an immunogical reactive hapten such as fluorescein and at the same time retain biological and binding activity.

The invention makes use of many available anti-hapten antibodies which specifically recognize a hapten-conjugated binding entity or ligand (hapten-ligand) in a complex mixture of other compounds which are naturally devoid of the hapten. The hapten-ligand is presented in excess to the substrate to which it binds. After binding, excess hapten-ligand is washed off, and all bound hapten-ligand is solubilized with or without solubilized substrate components. The solubilized mixture is applied to a membrane support directly or is separated by electrophoresis and then applied to a membrane support. The included membrane-bound hapten-ligand is detected by treatment of the membrane with anti-hapten antibody and then by an enzyme-conjugated-antibody to the anti-hapten antibody. The amount of resultant membrane-associated localized enzyme is determined by incubation with a color or light-producing substrate for that enzyme. For maximum sensitivity, a light-producing substrate is applied and the enzyme is detected by enhanced chemi-luminescence. A series of known amounts of pure hapten-ligand can be applied to the membrane support, or can be separated by electrophoresis and applied to the membrane support, and similarly detected, to determine a signal to dose standard curve which can be used to ascertain the amount of hapten-ligand in the unknowns. Thus, the system lends itself to very precise and user-defined standardization. The two-antibody incubation steps amplify the signal so that in combination with enhanced chemi-luminescence, very low levels of hapten-ligand can be detected. When used this way, the system can be used to measure ligand binding to cell surfaces without the need for radio-labeled ligand. Another feature of the system is that all of the reagents required are stable and have long shelf-lifes. The system is a low-cost, non-hazardous, sensitive, non-radioactive, precisely standardized method for determining the binding of compounds to substrates. In particular, the method lends itself to the measurement of hapten-conjugated protein binding to cell and tissue surfaces. Specifically, the method has been perfected for the use of measuring fluorescein-conjugated transferrin, fluorescein-conjugated concanavalin A, fluorescein-conjugated annexin-V, fluorescein-conjugated avidin, and fluorescein-conjugated insulin binding to tissue culture cell surfaces. This invention not only offers a novel non-radioactive method for assessing ligand binding to cell surfaces, but can be used to quantitate the binding of any recognizable hapten-containing binding factor to any surface, providing that the factor can be subsequently removed, (and perhaps separated by electrophoresis; optional), and bound to a membrane support.

DETAILED DESCRIPTION OF THE INVENTION

Figure 1:
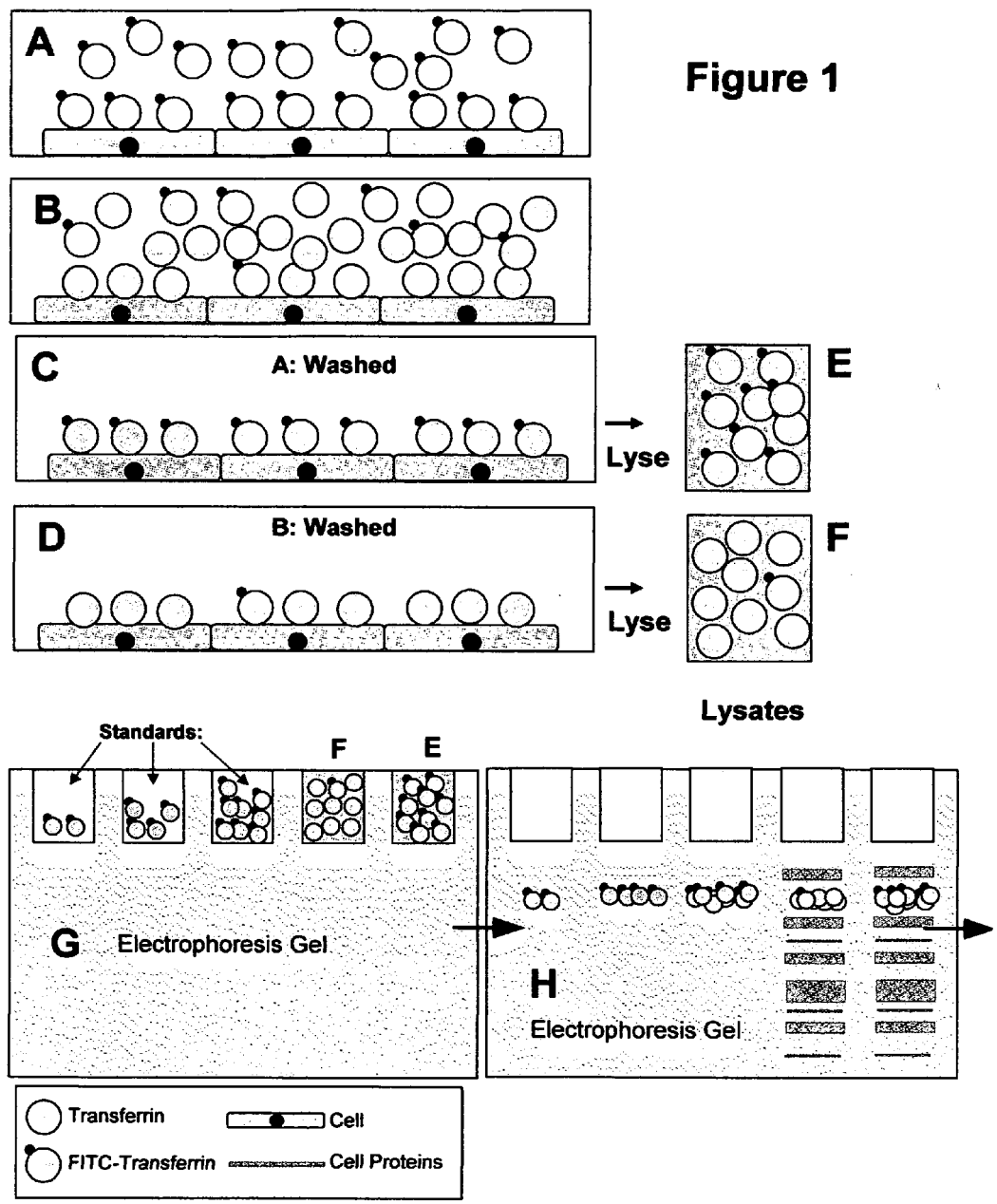
FIGS. 1A-1N show a schematic of the strategy of the assay, illustrating the measurement of the binding of FITC-transferrin (FITC-Tf) to cell surfaces.
Figure 1:
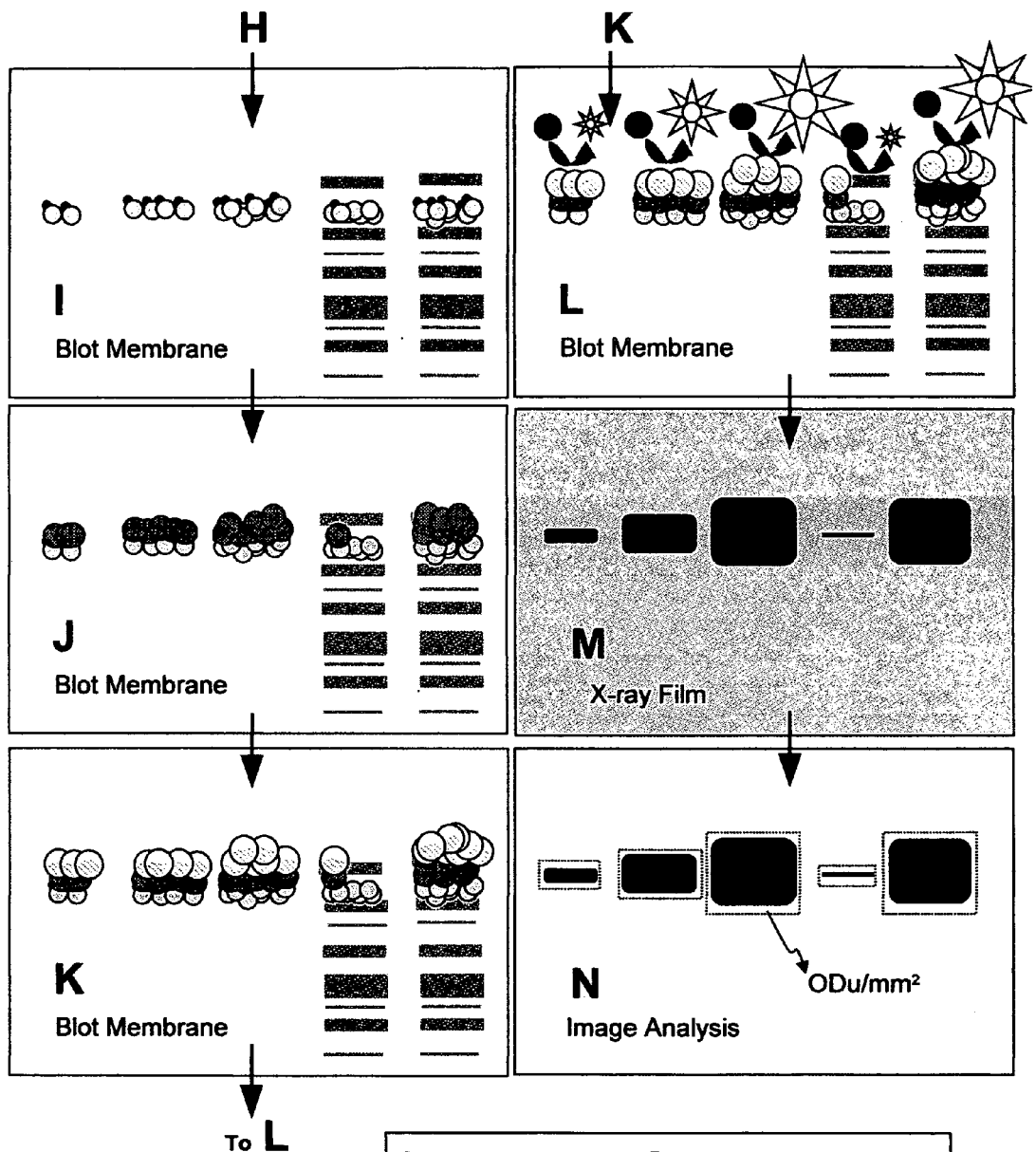

The object of the present invention is to provide a method for the sensitive non-radioactive assessment of ligand binding to insoluble surfaces. Specifically, the method developed measures the binding of transferrin, concanavalin-A, avidin, annexin-V, and insulin to cell surfaces. The basic detailed method using fluorescein-conjugated transferrin as a detectable antibody-recognizable hapten tracer follows. Specific alterations of this procedure for other ligands follow.

Fluorescein-conjugated iron-saturated (holo) human transferrin (FITC-Tf) was obtained from commercial sources. Cultured cells to be measured were grown to 50-60% confluence in 12 well plates. Cells were incubated with serum-free minimal essential media (alpha modification; $\alpha$-MEM) for 12 h and then again with fresh $\alpha$-MEM for another 12 h. The cell number in three wells was determined by trypsinization of those cells followed by enumeration on a cell counter. Media in remaining wells was replaced with 1 ml binding buffer (BB) which consisted of: 25 mM HEPES in $\alpha$-MEM containing 2 mg/ml of bovine serum albumin (BSA); pH 7.5. The cell wells were then allowed to equilibrate to 4° C. in a refrigerator. Sets of 5 replicate wells received increasing amounts of FITC-Tf, from 0.06 to 2.0 µg/ml final FITC-Tf. Two wells of each FITC-Tf concentration set then received unlabeled holo human transferrin so that the final [Tf]=100 µg/ml. After a 2 h incubation at 4° C., all media was saved (=unbound samples), and the wells were all washed 4 times by the addition and drainage of 1 ml of 4° C. PBS. All wells then received 0.5 ml of an RIPA cell lysing solution which consisted of PBS containing 1% v/v NP-40, 0.5% v/v deoxycholic acid, 0.1% v/v SDS, 100 µg/ml phenylmethyl sulfonyl chloride, and 0.1 TIU/ml Aprotinin. Cells were incubated with the lysing solution for 30 min at 4° C. and all lysates were pipetted into separate 1.5 ml conical tubes. The tubes were centrifuged at 5,000×g for 10 min and 400 uL of each supernatant was transferred to a fresh tube. All of these tubes received 166 uL of a 4× concentrate SDS-PAGE treatment solution, and were treated at 95° C. for 10 minutes.

Treated samples were loaded onto a 12×12 cm 10% acrylamide SDS-PAGE electrophoresis gel (150 uL/sample) and electrophoresed at 40 mA constant current until the dye front was 1 cm from the bottom of the gel. The gel was equilibrated in a transfer buffer of 48 mM Tris, 39 mM glycine. A 14×14 cm nitrocellulose membrane was equilibrated in transfer buffer and the gel and membrane assembled into a transfer apparatus and immersed in transfer buffer. Gel components were transferred to the membrane at a constant voltage of 40 V for 1.5 h.

The membrane was blocked at 4° C. overnight in a block solution consisting of Tris buffered saline (TBS: 25 mM Tris, 0.15 M NaCl, pH 7.8) containing 0.1% tween 20 and 5% w/v non-fat dry milk. The membrane was incubated with 1:1000 rabbit anti-FITC in block solution for 2 h at 25° C., and washed three times (20 min each) with 50 ml TBS. The membrane was incubated with 1:2000 horseradish peroxidase (HRP)-conjugated goat anti-rabbit IgG for 2 h at 25° C. and washed again. Each membrane was covered with an enhanced chemiluminescence (ECL) substrate for HRP, was wrapped in plastic, and was loaded into an X-ray film cassette along with an 8×10 inch piece of photographic film. The film was developed after 1 min exposure and an additional film was added which was developed after 20 min exposure. Bands produced on the film were quantified using an imager.

Unbound samples are run similarly to cell lysate samples. Typically, these have to be diluted 1:10-1:100 in SDS-PAGE treatment solution prior to electrophoresis, to produce a signal within a readable range. The assay is standardized by loading known amounts of pure FITC-Tf onto an electrophoresis gel and repeating all of the above procedures. The signal returned from the imager is plotted against the amount of FITC-Tf contained in the band and a standard curve is constructed to calculate the amounts of FITC-Tf bound by the cells.

A schematic of the strategy of the assay is shown in FIG. 1. A cell monolayer is exposed to a solution of FITC-Tf (FIG. 1A) or FITC-Tf plus an excess of unlabeled Tf (FIG. 1B). In either case, 3 molecules of Tf bind per cell. When washed and lysed (FIG. 1C), cells from FIG. 1A produced a lysate containing 9 molecules of FITC-TF (FIG. 1E) whereas cells from FIG. 1B produce a lysate containing 1 molecule of FITC-Tf (FIG. 1D, FIG. 1F). In FIG. 1H, both samples are electrophoresed and the gels blotted (FIG. 1I). With the cells from FIG. 1A, 9 molecules of FITC-Tf are present in the 70,000 molecular weight region of the blot; when this blot is incubated with rabbit anti-FITC and then with goat anti-rabbit-IgG-HRP, a large band is seen (FIG. 1J, FIG. 1K, FIG. 1L). With the cells from FIG. 1B, only one molecule of FITC-Tf is present on the blot and a minimal band is seen on the blot after ECL (FIG. 1J, FIG. 1K, FIG. 1L).

Figure 2:
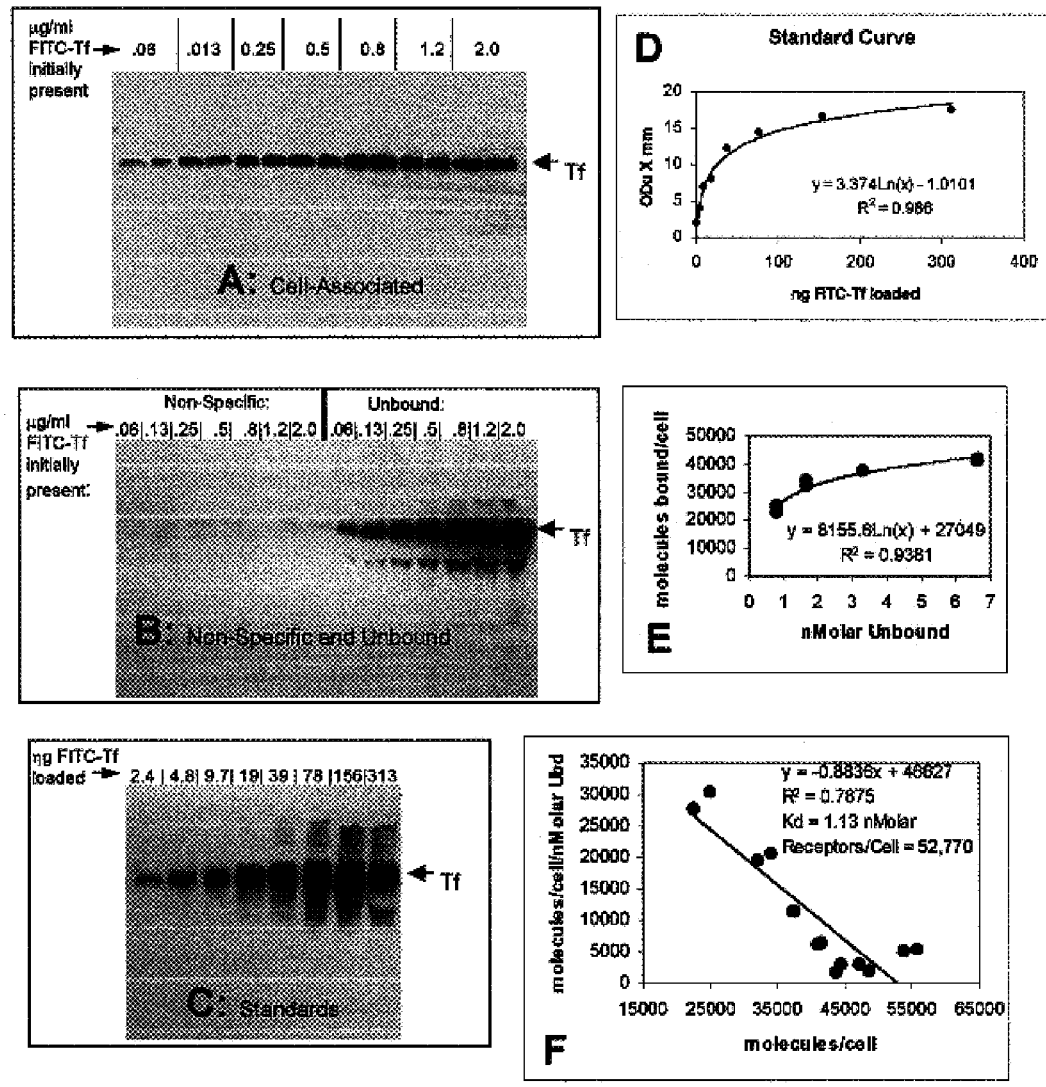
FIGS. 2A-2F show reproductions of actual enhanced chemiluminescence films of signals from electrophoretically separated cell lysates and standards, and the graphical analysis of the luminescence data, obtained when analyzing the binding of FITC-Tf to cell surfaces.

Reproductions of actual enhanced chemiluminescence films obtained when this assay was performed are shown in FIG. 2. FIG. 2A shows the measurement of FITC-transferrin (FITC-Tf) binding to MTLn2/TfR cells. Cells at 50-60% confluency growing in 12 well plates were serum-starved, then treated at 4° C. with increasing levels of FITC-Tf. After 2 h, cells were washed, lysed, and equal cell equivalents were electrophoresed, blotted, incubated with goat anti-FITC, then with anti-goat-HRP and an HRP ECL substrate. The blot was then analyzed using an imager. FIG. 2A shows results from lysates from cell exposed to the concentration of FITC-TF listed above the blot. FIG. 2B (left side) shows results from lysates from cells treated as in FIG. 2A, but also with 100 µg/ml of unconjugated Tf. FIG. 2C shows results from a blot treated as in FIG. 2A but loaded with pure FITC-TF standards in the amounts (in ηg) indicated on the top. The pure FITC-Tf samples were electrophoresed, blotted, and measured using the two antibodies mentioned in FIG. 2A, followed by ECL. FIG. 2D shows results from the quantification of FIG. 2C using an imager, indicating the type of standard curves achievable.

The binding of annexin V to cell surfaces has been recognized as an indicator of early apoptosis (Zhang et. al., 1997). With conventional procedures, cells are removed from plates, treated with FITC-annexin V, and analyzed by FACS. The removal of cells from tissue culture plates using conventional trypsin or EDTA reagents can in itself induce cell stress, apoptosis, and cellular annexin V binding (Darzynkiewicz et. al., 1998; LeGall et. al., 2000). Therefore, the conventional use of annexin V binding as a measure of apoptosis in adherent cells is problematic. In contrast, this invention would measure the binding of FITC-annexin V to adherent cultured cells in situ (FIGS. 3 and 4), where binding and washing occur first, before the cells are removed from plates for analysis. Therefore, the amount of FITC-annexin V detected would accurately represent that bound by cells in their natural culture environment. Thus, the method outlined in this invention circumvents conventional problems and provides for a more authentic measure of natural cellular annexin V binding.

Figure 3:
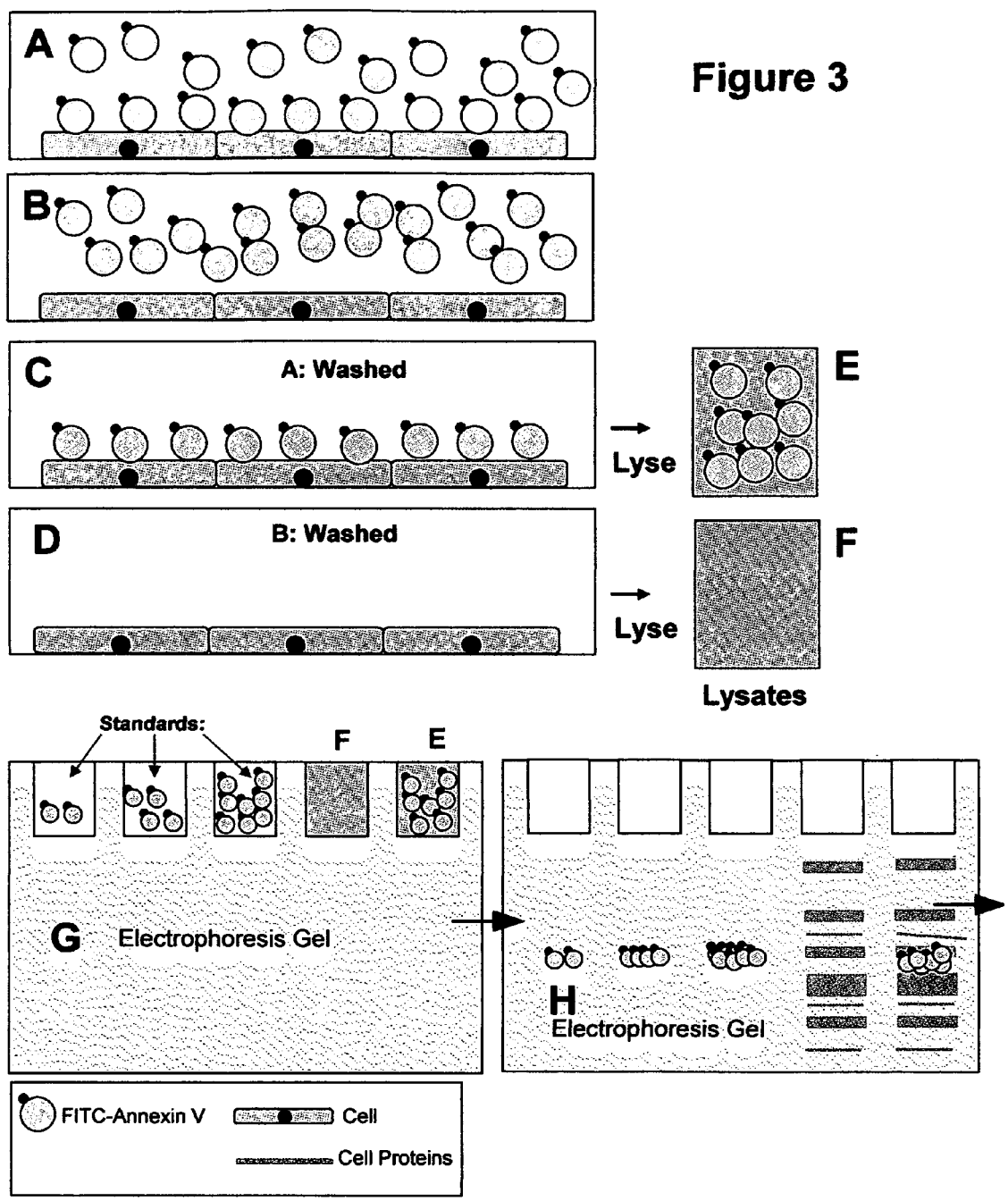
FIGS. 3A-3N show a schematic of the strategy of the assay, illustrating the measurement of cellular apoptosis by analyzing the binding of FITC-annexin-V to cell surfaces.
Figure 3:
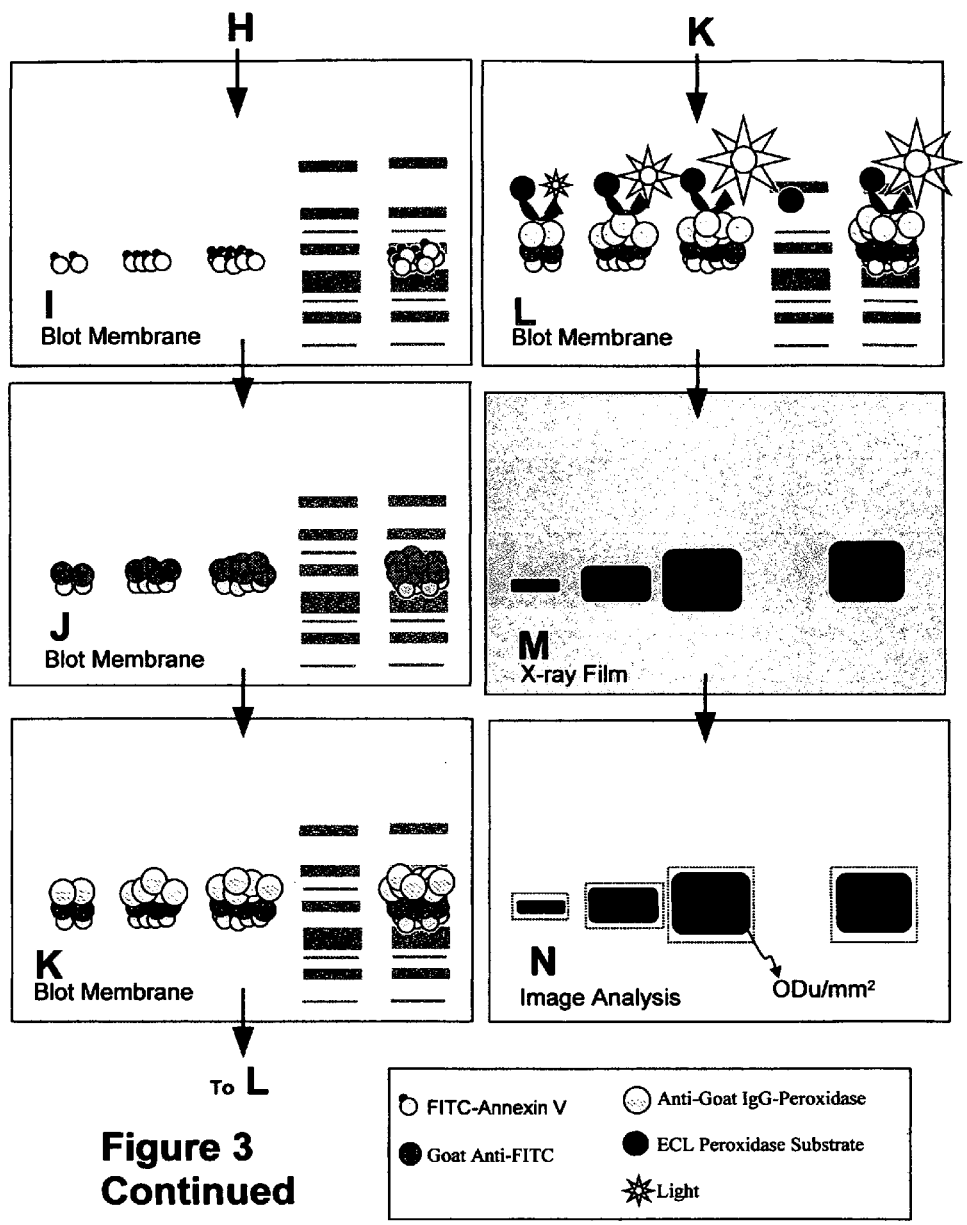

A schematic of the strategy of the assay when used to detect apoptotic cells is shown in FIG. 3. Cells in early apoptosis are known to bind the protein Annexin V whereas normal cells bind little or none of this protein. Cells in apoptosis (FIG. 3A) or normal non-apoptotic cells (FIG. 3B) are exposed to a solution of FITC-Annexin V. When washed (FIG. 3C, FIG. 3D) and lysed (FIG. 3E, FIG. 3F), cells from FIG. 3A produced a lysate containing FITC-Annexin V (FIG. 3E) whereas cells from FIG. 3B produce a lysate containing no FITC-Annexin V (FIG. 3F). In FIG. 3G and FIG. 3H, both samples are electrophoresed and the gels electro-blotted (FIG. 3I). With the cells from FIG. 3A, the FITC-Annexin V molecules are present in the 33,000 molecular weight region of the blot. When this blot is incubated with anti-FITC and then with anti-goat-IgG-HRP, HRP is localized to the 33 Kd region of the blot (FIG. 3J, FIG. 3K) and the HRP-containing bands are detected on photographic film using an HRP chemiluminesent substrate (FIG. 3L, FIG. 3M). This produces a band on the film at 33 Kd (FIG. 3M). With the cells from FIG. 3B, no FITC-Annexin V is present on the blot (FIG. 3I), the initial antibody and therefore the second antibody do not bind (FIG. 3J, FIG. 3K), no light is produced upon incubation with an HRP chemiluminesent substrate (FIG. 3L, FIG. 3M), and no band is seen on the film (FIG. 3M).

Figure 4:
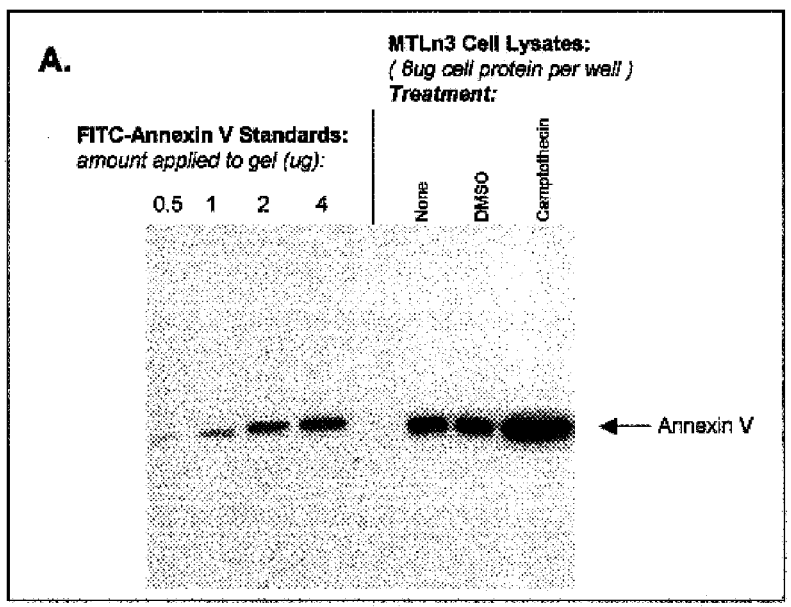
FIGS. 4A-4C show a reproduction of the actual enhanced chemiluminescence film of signals from electrophoretically separated cell lysates and standards, and the graphical analysis of the luminescence data, obtained when analyzing the binding of FITC-annexin-V to cell surfaces.
Figure 4:
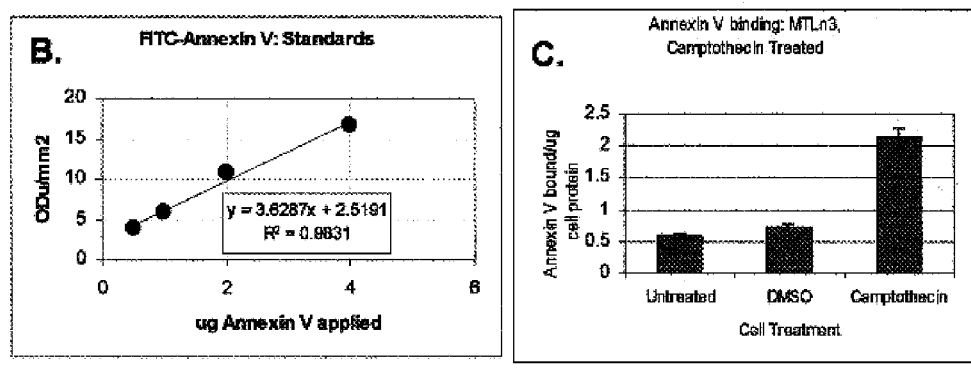

FIG. 4 shows the results obtained when this assay was used to measure the binding of FITC-Annexin V to rat MTLn3 mammary adenocarcinoma cells, as described in FIG. 3. The cells were grown to confluence in six well plates. Cells were induced to apoptose by treatment with 4 ug/ml Camptothecin (dissolved in DMSO). Controls received DMSO only. After 24 h, wells were washed three times with and equilibrated in 1 ml binding buffer (25 mM HEPES, 0.15 M NaCl, 2.5 mM $CaCl_2$, pH 7.5). FITC-Annexin V was added to 50 ηg/ml and the cells were incubated for 30 min at 25° C. Cells were then washed extensively with binding buffer, and lysed in 1 ml of RIPA lysing solution. The lysates were centrifuged at 5,000×g for 5 min., and the supernatants were separated by SDS-PAGE. Also run on the same gel were increasing levels of pure FITC-Annexin V. Separated proteins were blotted onto a nitrocellulose membrane which was blocked and then incubated with rabbit anti-FITC and then goat anti-rabbit IgG-HRP. HRP containing bands were detected by ECL. A scan of the photographic film is shown in FIG. 4A. Results of the quantification of the standards is shown in FIG. 4B. The curve from FIG. 4B was used to calculate Annexin V bound by the cells, the results of which are shown in FIG. 4C. The results indicate greater Annexin V binding by the camptothecin treated cells.

Figure 5:
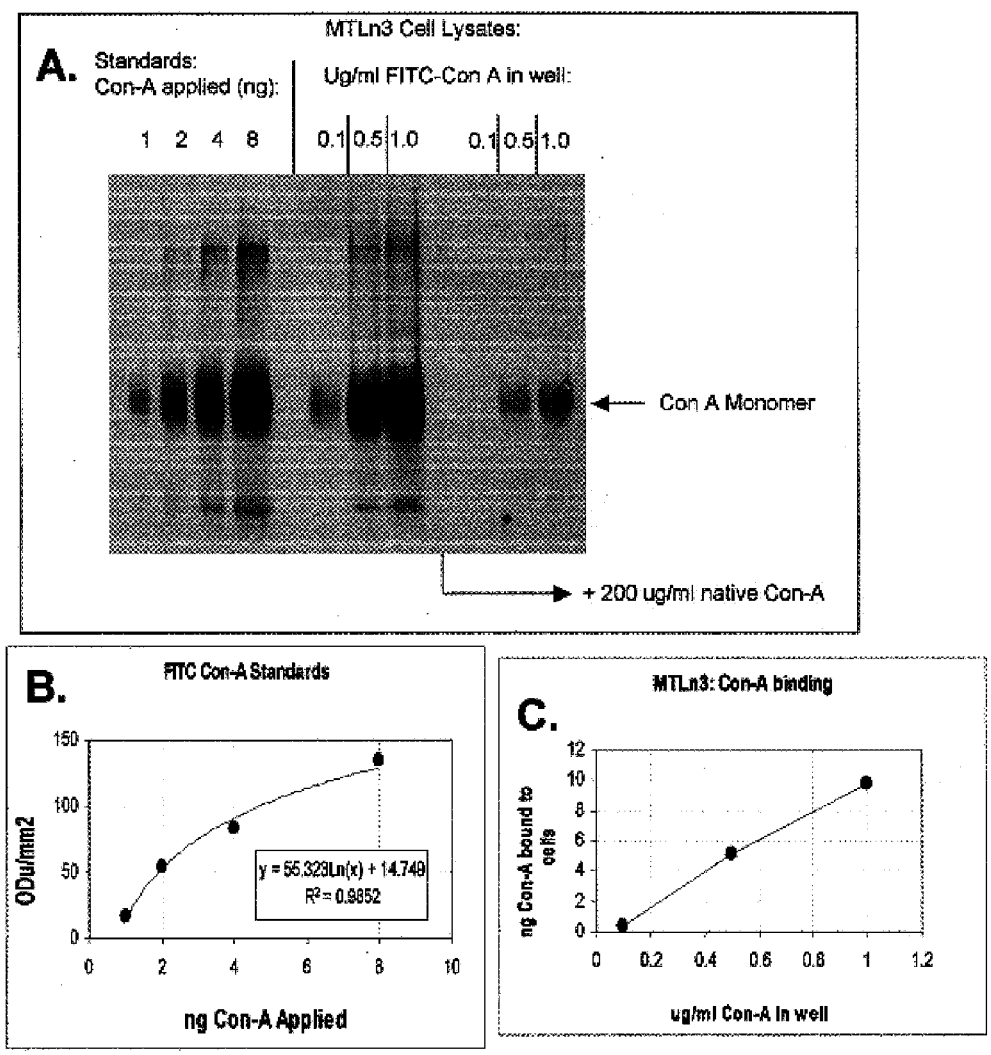
FIGS. 5A-5C show a reproduction of the actual enhanced chemiluminescence film of signals from cell lysates and standards, and the graphical analysis of the luminescence data, obtained when analyzing the binding of FITC-conjugated concanavalin A to cell surfaces, after separation by electrophoresis.

FIG. 5 shows the results obtained when this assay was used to measure the binding of FITC-Concanavalin A (Con A) to rat MTLn3 mammary adenocarcinoma cells. The cells were grown to confluence in six well plates. The growth media was replaced with a binding buffer consisting of 25 mM HEPES buffered MEM containing 3 mg/ml liquid gelatin (as a carrier and blocking protein), at pH 7.5. The cultures were taken to 4° C. and FITC-Con A was added to replicate wells so that the final concentrations of FITC-Con A were 0.1, 1.0, and 10.0 μg/ml. One well of each FITC-Con A concentration also received 200 μg/ml of native (un-conjugated Con A). The cells were incubated for 2 h at 4° C., washed extensively with PBS, and lysed in 800 μL of RIPA lysing solution. The lysates were centrifuged at 5,000×g for 5 min., and the supernatants were separated by SDS-PAGE. Also run on the same gel were increasing levels of pure FITC-Con A. Separated proteins were blotted onto a nitrocellulose membrane which was blocked and incubated with rabbit anti-FITC and then goat anti-rabbit IgG-HRP. HRP containing bands were detected by ECL. A scan of the film is shown in FIG. 5A. Results of quantification of the standards is shown in FIG. 5B. The curve from FIG. 5B was used to calculate specific Con A bound by the cells, the results of which are shown in FIG. 5C.

Figure 6:
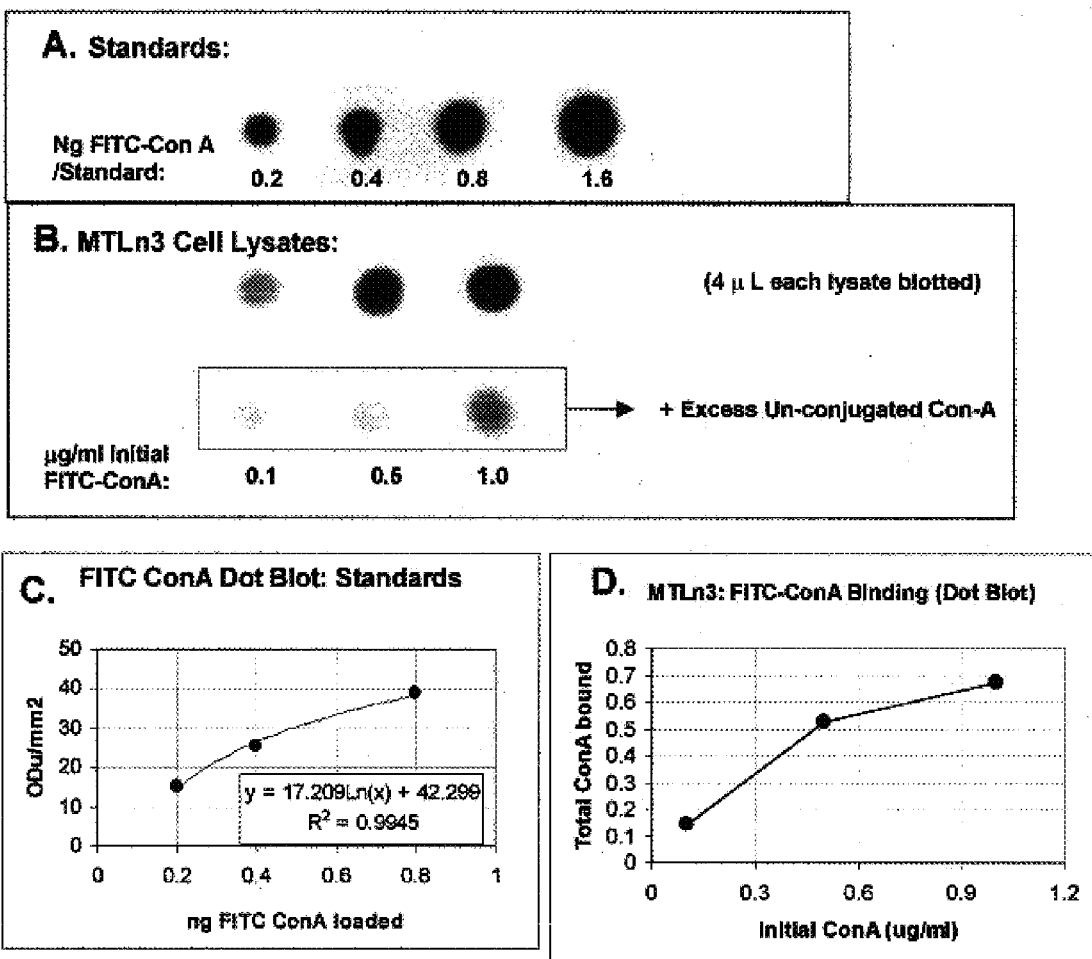
FIGS. 6A-6D show a reproduction of the actual enhanced chemiluminescence films of signals from cell lysates and standards, and the graphical analysis of the luminescence data, obtained when analyzing the binding of FITC-conjugated concanavalin A to cell surfaces by dot blotting, without preliminary separation.

FIG. 6 shows results obtained when the samples from FIG. 5 were analyzed by a dot blot procedure. For the standards, increasing volumes (2, 4, 8, and 16 μL) of a 100 ηg/ml FITC-Con A solution were applied to a nitrocellulose membrane. For the lysates, 4 μL of lysates from cells treated with 0.1, 0.5, and 1.0 μg/ml FITC Con A (with or without an excess native Con A) were applied to the membrane. The membrane was blocked, incubated with rabbit anti-FITC, then with goat anti-rabbit IgG-HRP, and HRP-containing sites detected with ECL (FIG. 6A, FIG. 6B). The dots were quantified using an imager. Data from the standards (FIG. 6A, FIG. 6C) were used to determine the amount of Con A bound by the cells (FIG. 6B, FIG. 6D). This displays the usefulness of the technique in a dot-blot procedure, where the SDS-PAGE and electro-blotting steps are eliminated.

Figure 7:
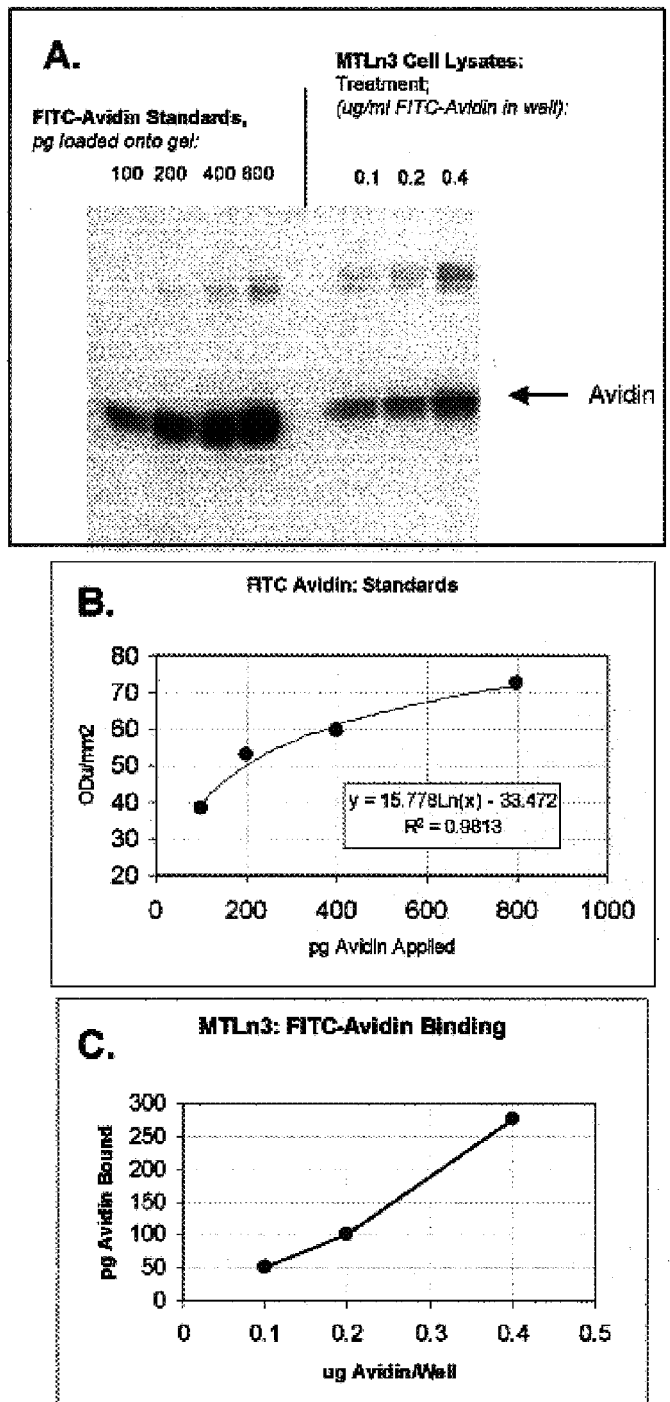
FIGS. 7A-7C show a reproduction of the actual enhanced chemiluminescence film of signals from electrophoretically separated cell lysates and standards, and the graphical analysis of the luminescence data, obtained when analyzing the binding of FITC-avidin to cell surfaces.

FIG. 7 shows results obtained when this assay was used to measure the binding of FITC-Avidin to rat MTLn3 mammary adenocarcinoma cells. The cells were grown to confluence in six well plates. The growth media was replaced with a binding buffer consisting of 25 mM HEPES buffered MEM containing 3 mg/ml liquid gelatin (as a carrier and blocking protein), at pH 7.5. The cultures were taken to 4° C. and FITC-Avidin was added to replicate wells so that the final concentrations of FITC-Avidin were 0.1, 0.2, and 0.4 μg/ml. The cells were incubated for 2 h at 4° C., washed extensively with PBS, and lysed in 1 ml of RIPA lysing solution. The lysates were centrifuged at 5,000×g for 5 min., and the supernatants were separated by SDS-PAGE. Also run on the same gel were increasing levels of pure FITC-Avidin. Separated proteins were blotted onto a nitrocellulose membrane which was blocked and incubated with rabbit anti-FITC and then goat anti-rabbit IgG-HRP. HRP containing bands were detected by ECL. A scan of the photographic film is shown in FIG. 7A. Results of quantification of the standards is shown in FIG. 7B. The curve from FIG. 7B was used to calculate specific Avidin bound by the cells, the results of which are shown in FIG. 7C.

Figure 8:
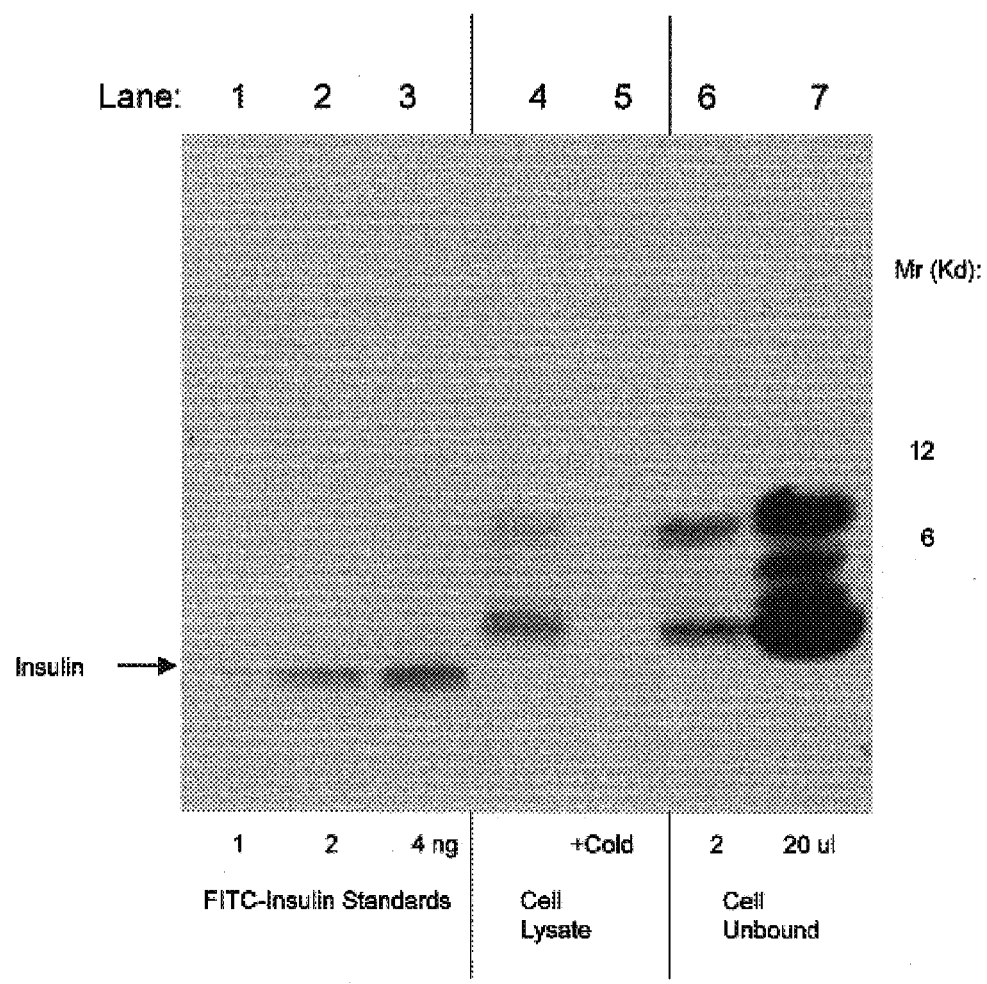
FIG. 8 shows a reproduction of the actual enhanced chemiluminescence film of signals from electrophoretically separated cell lysates and standards obtained when analyzing the binding of FITC-insulin to cell surfaces.

FIG. 8 shows the results obtained when this assay was used to measure the binding of FITC-Insulin to human K562 erythroleukemia cells. Logarithmically growing cells in suspension culture were collected by centrifugation and washed twice by suspension in and centrifugation from a binding buffer consisting of alpha-MEM containing 5 mg/ml BSA and 25 mM HEPES (pH 7.5). Cells were adjusted to a density of $2 \times 10^6$/ml (in binding buffer), and were equilibrated to 4° C. To 1 ml of cell suspension was added 20 μl of 1 mg/ml FITC-Insulin (in binding buffer; final concentration=20 μg/ml). An additional tube also received non-conjugated Insulin at a level of 200 μg/ml. Cell suspensions were incubated for 2 h at 4° C. while rotating slowly, and the cells were collected and washed three times by suspension in and centrifugation from binding buffer. Cell pellets were lysed in 0.4 ml/tube of Schagger-Von Jagow (SVJ) electrophoresis system treatment solution and treated at 95° C. for 5 min. Lysates (100 μl each) were separated by SDS-PAGE n according to Schagger-Von Jagow (see Schagger, H., and Von Jagow, G., *Analytical Biochemistry* 166:368-379, 1987) along with FITC-Insulin standards, and treated aliquots of the cell-unbound incubation mixture. Gel components were transferred to nitrocellulose and membrane-associated FITC detected as described with other ligands. In FIG. 8, a scan of the ECL film is shown. Increasing signal is returned for increasing loads of FITC-insulin in the standards (FIG. 8, Lanes 1-3). The FITC-insulin bound by the cells is easily observed (FIG. 8, Lane 4), and this is reduced significantly when excess un-conjugated insulin was present (FIG. 8, Lane 5). This procedure consistently displays higher molecular weight forms of insulin formed after application to cells, perhaps due to the presence of insulin binding proteins (FIG. 8, Lanes 4-7).

The assay could be used to verify the hybridization of biotin-labeled DNA to other DNA molecules. In one scenario, biotin-labeled PCR products are hybridized to an immobilized DNA probe which specifically recognizes the desired PCR product (among a mixture of non-specific products). After binding, the bound PCR product is released through heat de-naturation, is separated by agarose electrophoresis, electro-blotted to nytran, and is detected by incubation with species-x anti-biotin followed by incubation with anti-species-x IgG-HRP and ECL. The final result yields a major band at the expected bp size of the PCR product. Any non-specific bands of different size can be ignored during analysis of the film by an image analyzer. As with the above stated protein procedures, the proper molecular weight of the desired product is verified.

The replacement of electrophoresis with dot-blot techniques is possible. This would require that the only immune-recognizable conjugated component present prior to dot-blotting would be the desired product and/or absolutely minimal interaction of either antibody with non-specific sample components General applications: The assay strategy can apply to any ligand conjugated with a compound which can be specifically recognized by an antibody. In particular, anti-digoxygenin, anti-rhodamine and anti-biotin antibodies exist which would recognize ligands conjugated with those compounds. The material to which the ligand binds to can be other than cells. Any particles or other insoluble material can serve as the binding surface. Centrifugation and re-suspension of suspended particulate binding substrates would serve as a method for washing those of unbound ligand. The current method requires that the bound ligand be removed from the binding surface so that it can be separated by electrophoresis. It must also bind to a conventional transfer membrane for detection with the antibody. Other specific applications accomplished to date include the study of the binding of FITC-conjugated concanavalin A to cells, the study of the binding of Avidin to cells, and the study of the binding of Annexin-V to cells. With the latter protein, this assay could be utilized to assess cellular apoptosis without the need for a FACS analyzer.

Conclusion: the invention is a procedure for measuring the binding of an entity (ligand) to a surface by using a hapten-conjugated version of the ligand (hapten-ligand), where the hapten is recognizable by an antibody. An excess of the hapten-ligand is presented to the binding surface and excess (unbound) hapten-ligand is washed off. Bound hapten-ligand is then solubilized (removed) and applied to a membrane support or separated by electrophoresis and applied to a membrane support. The membrane-bound hapten-ligand is detected by application of an enzyme-conjugated antibody to the hapten; or by application of an antibody to the hapten followed by application of an enzyme-conjugated antibody to the anti-hapten antibody. The resultant membrane-associated enzyme is detected and quantified by the application of a color or light-producing substrate which reacts with the enzyme. This assay method has the advantages of providing verification of the molecular weight of the binding substance (ligand) via the electrophoresis step. It eliminates the need for radioactive materials. The procedure provides for high sensitivity detection as the dual antibody incubation steps amplify the signal significantly. The procedure allows for easy standardization as different user-definable levels of a standard solution of the Hapten-ligand can be simultaneously applied to the electrophoresis gel or to the dot-blot or slot-blot membrane.

The invention claimed is:

1. A method for the quantification of ligand binding to a surface, using hapten-conjugated ligands, comprising:
   (a) applying a hapten-ligand, comprising a ligand possessing an antibody-recognizable hapten, to said surface, and,
   (b) waiting for a period of time, so as to allow a binding of said hapten-ligand to said surface, thereby producing bound ligand, and,
   (c) removing any unbound hapten-ligand, from said surface, and,
   (d) solubilizing said bound ligand, thereby producing a lysate, and,
   (e) applying separately onto a membrane,
      (1) said lysate, and,
      (2) a plurality of standards, comprising solutions containing increasing levels of known amounts of the hapten-ligand,
      thereby producing membrane-bound hapten-ligand and,
   (f) applying to said membrane,
      (1) an enzyme-conjugated antibody to specific for said hapten, and,
      (2) a color or light-producing substrate that contacts the enzyme on said enzyme-conjugated antibody,
      thereby producing a signal, and,
   (g) comparing said signal arising from said enzyme associated with said membrane-bound hapten-ligand arising from said standards, to the known amount of hapten-ligand contained in said standards, thereby producing a standard curve, and,
   (h) quantifying the amount of said hapten-ligand originally bound to said surface, by quantifying the amount of the hapten-ligand contained in said membrane-bound hapten-ligand arising from said lysate, by comparing said signal arising thereof to said standard curve and,
   whereby the use of radio-labeled ligand is avoided.

2. The method of claim 1, wherein said method for the quantification of ligand binding to a surface, is further comprising:
   (a) applying to said surface of claim 1 step (a), said ligand which is further comprising a mixture of:
      (1) said hapten-ligand, and,
      (2) un-conjugated ligand, comprising said ligand which does not possess said hapten, and,
   (b) verifying the specific binding of said hapten-ligand to said surface, by comparing said signal from claim 1 step (f) step (2) arising from said lysate containing both said hapten-ligand, and said un-conjugated ligand to said signal arising from said lysate containing said hapten-ligand only.

3. The method of claim 1, wherein the quantification of ligand binding to a surface, is further comprising:
   (a) separating said lysate of claim 1 step (d) by electrophoresis, and,
   (b) separating said standards of claim 1 step (e) step (2), by electrophoresis, and,
   (c) applying separated lysate, and separated standards to said membrane and,
   (d) verifying the location of said hapten-ligand, contained in separated lysates, on said membrane, by comparing said signal arising thereof to the location of said signal arising from separated standards, on said membrane.

4. The method of claim 3 wherein said method of electrophoresis is selected from the group consisting of SDS-PAGE, electrophoresis according to Schagger Von Jagow, and agarose electrophoresis.

5. The method of claim 1 step (f) step (1), wherein the applying of an antibody to said membrane is further comprising:
   (a) applying an anti-hapten antibody, comprising an antibody specific for said hapten, to said membrane and,
   (b) applying an enzyme-conjugated antibody specific for said to anti-hapten antibody, to said membrane.

6. The method of claim 1, wherein said surface includes biological cells.

7. The method of claim 1, wherein said hapten includes compounds which can be specifically recognized by an antibody.

8. The method of claim 1, wherein said hapten is selected from the group consisting of, fluorescein, biotin, rhodamine, and digoxygenin.

9. The method of claim 1, wherein said ligand is a biological factor.

10. The method of claim 1, wherein said ligand is a protein.

11. The method of claim 10, wherein said protein is selected from the group consisting of transferrin, concanavalin A, avidin, annexin V, and insulin.

12. The method of claim 1, wherein said ligand is DNA.

13. The method of claim 1 step (e), wherein the applying of said lysate and said standards onto said membrane is achieved by a blotting method.

14. The method of claim 13, wherein said blotting method is selected from the group consisting of electroblotting, dot blotting, slot blotting, and Western blotting.

15. The method of claim 1 step (e), wherein said membrane includes transfer membranes.

16. The method of claim 1 step (e), wherein said membrane is selected from the group consisting of protein binding membranes, and DNA binding membranes.

17. The method of claim 1 step (e), wherein said membrane is selected from the group consisting of nitrocellulose, and nylon membranes.

18. The method of claim 1 step (f), wherein said enzyme is horseradish peroxidase.

19. The method of claim 1 step (f) step (2), wherein the quantifying of said signal, arising from said light producing substrate, on said membrane is further comprising:
   (a) placing said membrane in contact with photographic film, and,
   (b) analyzing said signal on said photographic film using an imager.

20. The method of claim 1 step (f), wherein the applying to said membrane further comprises an initial applying to said membrane of a block solution.

* * * * *